(12) United States Patent
Kondo

(10) Patent No.: US 6,849,043 B2
(45) Date of Patent: Feb. 1, 2005

(54) SUCTION VALVE FOR ENDOSCOPE USE

(75) Inventor: Mitsuo Kondo, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 51 days.

(21) Appl. No.: 10/389,884

(22) Filed: Mar. 18, 2003

(65) Prior Publication Data

US 2003/0181787 A1 Sep. 25, 2003

(30) Foreign Application Priority Data

Mar. 22, 2002 (JP) ......................................... 2002-082163

(51) Int. Cl.$^7$ .................................................. A61B 1/12

(52) U.S. Cl. ..................................................... 600/159

(58) Field of Search .......................... 600/159; 604/6.1, 604/33, 99.01, 167.04

(56) References Cited

U.S. PATENT DOCUMENTS 5,840,015 A * 11/1998 Ogino ........................ 600/159

FOREIGN PATENT DOCUMENTS

JP 07-008448 1/1995

* cited by examiner

Primary Examiner—Beverly M. Flanagan
(74) Attorney, Agent, or Firm—Rabin & Berdo, P.C.

(57) ABSTRACT

A suction valve for an endoscope use includes a valve casing which is set up in the control portion of an endoscope and is connected with a suction side path having an opening as a suction inlet at the tip distal end of the insertion portion of the endoscope and is also connected with a suction source side path connected with a negative pressure generation source, and a valve member which is fitted up in the valve casing to be allowed to make a slide motion inside thereof and is constituted such that it is able to switch the state in which the suction side path is cut off from the suction source side path to the state in which the suction side path is in communication with the suction source side path or vice versa in correspondence with the position of the valve member in the valve casing, wherein a groove is formed in the outer peripheral surface of the valve member in contact with the inside of the valve casing. With this, foreign substances for instance body fluids and others sticking to a gap between the valve casing and the valve member are driven into the groove formed in the outer peripheral surface of the valve member by the slide motion of the valve member, thus the slide friction being prevented from increasing and further, enabling the suction switching control to be carried out stably and smoothly.

13 Claims, 9 Drawing Sheets

SUCTION VALVE FOR ENDOSCOPE USE

BACKGROUND OF THE INVENTION

The present invention relates to a suction valve built in an endoscope, especially an endoscope for medical use.

In general, the endoscope for use in the medical inspection of the somatic cavity and others is equipped with a suction mechanism for sucking up filthy matters, mucus and others staying in the somatic cavity. The suction mechanism of this kind is equipped with a suction path, of which one end opens as a suction inlet at the tip distal end of the insertion portion of the endoscope and the other end side is connected with a negative pressure generation source. If it is required to remove filthy matters, mucus, body fluids and others left in the somatic cavity, the negative pressure generation source operates to make a negative pressure suction force act on the inside of the suction path, thereby sucking up filthy matters, mucus and others staying in somatic cavity through the suction inlet at the tip distal end of the endoscope.

Now, referring to FIG. 7 schematically showing the constitution of the entirety of an endoscope, this endoscope 200 is constituted such that an insertion portion 204 is connected with a control portion 202 while a universal cord 206 branching off the control portion 202 is connected with the negative pressure generation source (not shown) and a light source device (not shown) as well.

The insertion portion 204 is provided with an insertion channel 208 capable of transferring medical treatment tools for instance a forceps and others for the exclusive endoscope use therethrough. The treatment tool insertion channel 208 is in communication with a treatment tool inducing inlet 210 which opens to the control portion 202.

As the treatment tool insertion channel 208 can be used also as a suction path, the tip opening of it is able to function as a suction inlet. This treatment tool insertion channel 208 joins to a suction side path 212 at a certain point inside the control portion 202.

The suction side path 212 communicates with a suction source side path 214 through a suction valve 216 provided in the control portion 202. In this way, a suction route is formed by the treatment tool insertion channel 208, the suction side path 212, and the suction source side path 214. The suction source side path 214 is provided inside the universal cord 206 and connected with the negative pressure source (not shown).

The suction valve 216 is a valve for controlling the change of the connection between the suction side path 212 and the suction source side path 214. FIG. 8 indicates an example of the constitution of the valve of this kind.

The suction valve 216 includes a valve casing 218 fitted to the control portion 202 of the endoscope 200, and a valve member 220 which is set up in the valve casing 218 so as to make a sliding motion in response to the push-down motion of a button 221.

An active blockade face 222 is formed in the outer peripheral surface around the lower part of the valve member 220 while a side through-hole 224 is formed on the upper side of the active blockade face 222. The bottom portion of the valve member 220 is kept open and communicated with the above side through-hole 224.

The suction side path 212 and the suction source side path 214 are connected together with the valve casing 218. With the sliding motion of the valve member 220, the suction side path 212 comes to communicate with the suction source side path 214 through the side through-hole 224 of the valve member 220, and it is cut off from the suction source side path 214 by the active blockade face.

As long as the endoscope is being used, the negative pressure generation source (not shown) is continuously kept in the powered condition. On one hand, while no suction control is carried out, the button 221 is not push downward as shown in FIG. 8. Consequently, the suction side path 212 is cut off from the suction source side path 214 by the active blockade face 222 of the valve member 220 while the negative pressure source comes to communicate with the atmosphere through the suction valve 216. To put it more concretely, the suction source side path 214 comes to communicates with the atmosphere through the side through-hole 224, an opening 232a formed in a spring seat member 232 for supporting a spring 226 energizing the button 221 and an air releasing groove 236, respectively. With this constitution, the suction inlet in communication with the suction side path 212 is held substantially in the non-loaded condition.

When executing the suction control, the valve member 220 of the suction valve 216 is pushed downward by using the hand fingers to make it slide downward along the casing 218. With this downward-motion of the valve 220 as shown in FIG. 9, the suction side path 212 comes to communicate with the suction source side path 214 through the side through-hole 224 of the valve member 220, thereby the negative sucking pressure generated by the negative pressure generation source coming to act on the suction side path 212.

In the suction valve for use in the endoscope of this kind, however, even if no suction control is carried out as shown in FIG. 8, it takes place under certain circumstances that foreign substances such as filthy matters, mucus, body fluids and others stick to the active blockade face 222 of the valve member 220. If the valve member 220 is moved to slide along the casing 218 as shown in FIG. 9, it takes place that the foreign substances like the above-mentioned comes in a slide portion, that is, a very narrow gap between the valve casing 218 and the active blockade face 222 of the valve member 220. This causes such a problem that the slide friction becomes large in the tiny gap between the valve casing 218 and the active blockade face 222 of the valve member 220.

Consequently, if the above slide friction becomes larger than the restoration force of the spring 226 prepared as means for energizing the valve member 220, it becomes hard for the valve member 220 to go back to its original position, which makes the smooth suction control impossible, eventually.

Accordingly, the invention has been made in view of the above-mentioned problem, and an object of it is to provide a novel and improved suction valve for use in the endoscope, which is able to make the suction switch control more stable and smooth.

SUMMARY OF THE INVENTION

In order to solve such a problem as described above, according to the first aspect of the invention, there is provided a suction valve for an endoscope use including a valve casing which is set up in the control portion of the endoscope and is connected with a suction side path having an opening as a suction inlet at the tip distal end of the insertion portion of the endoscope and is also connected with a suction source side path connected with a negative pressure generation source; a valve member which is fitted up in the valve casing to be allowed to make a slide motion inside thereof and is constituted such that it is able to switch the state in which the suction side path is cut off from the suction source side path to the state in which the suction side path is in communication with the suction source side path or vice versa in correspondence with the position of the valve member in the valve casing; and a groove formed in the outer peripheral surface of the valve member which comes in contact with the inside of the valve casing.

Furthermore, the above valve member may be constituted such that one state wherein the suction side path is cut off while the suction source side path is in communication with the atmosphere and the other state wherein the suction source side path is cut off from the communication with the atmosphere while the suction source side path is in communication with the suction side path are switched from one to the other or vise versa corresponding to the position of the valve member in the valve casing.

Still further, the above groove may be formed in an active blockade face which is formed in the outer peripheral surface of the valve member to cut off the suction side path.

Still further, an airtightness-holding member may be provided in order to hold the airtightness of a slide portion between the valve member and the valve casing, the airtightness-holding member being fitted into both ends of a part defined on the outer peripheral surface of the valve member to cut off the suction side path, and at least a groove is formed between the airtightness-holding members on the outer peripheral portion of the valve member.

Still further, it is preferable that the above groove is formed in the outer peripheral surface of the valve member and has a spiral-like or circumstance-like shape.

As the suction valve according to the invention is constituted as mentioned above, even if foreign substances for instance filthy matters, mucus, blood, body fluids and so forth in the somatic cavity are stuck on the outer peripheral surface of the valve member for instance the active blockade face, the foreign substances are driven into the groove formed in the active blockade face and comes to stay therein when pushing down the valve member for suction switching. Consequently, as the foreign substances are prevented from staying in the slide portion between the valve casing and the valve member, there is not caused increase in the slide friction, thus the stable and smooth suction switching being realized.

Still further, it is preferable that the groove is formed such that the nearer the groove approaches the suction source side path under the valve member, the wider the width of it becomes. As the foreign substances driven into the groove are moved in the direction of the suction source side path, a larger amount of the foreign substances can be stored inside the above groove.

Still further, the depth of the groove is twice as large as or more than a gap width between the valve casing and the outer peripheral surface of the of the valve member for instance the active blockade face cutting off the suction side path. With this, it becomes possible to more efficiently move and store the foreign substances stuck on the active blockade face.

Still further, it is preferable that the section of the groove has such a shape that the opening portion of it is made wider to the depth of the groove, for instance a trapezoidal shape, a curved shape and so forth. With this, in case of cleaning the valve member, the foreign substances stored in the groove can be removed with much ease by detaching the valve member from the valve casing.

Still further, a plurality of grooves may be formed to face in the direction vertical to the slide direction of the valve member. Still further, a plurality of grooves may be formed to face in the oblique direction with respect to the slide direction of the valve member.

Still further, a plurality of grooves may be formed to face in the direction vertical to the slide direction of the valve member and additionally at least a groove may be formed to face in the oblique direction such that it communicates with each of the above plural grooves. Still further, the groove may be formed along the slide direction of the valve member.

BRIEF OF DESCRIPTION OF THE DRAWINGS

The invention will now be describe in detail by way of some preferable embodiments of the invention with reference to the accompanying drawings, in which a like part having substantially identical function and constitution is indicated by a like reference numeral or character in order to omit a repetitive and redundant description thereabout. In the drawing.

DETAILED DESCRIPTION OF THE PREFERRED EMBODIMENT

Figure 1:
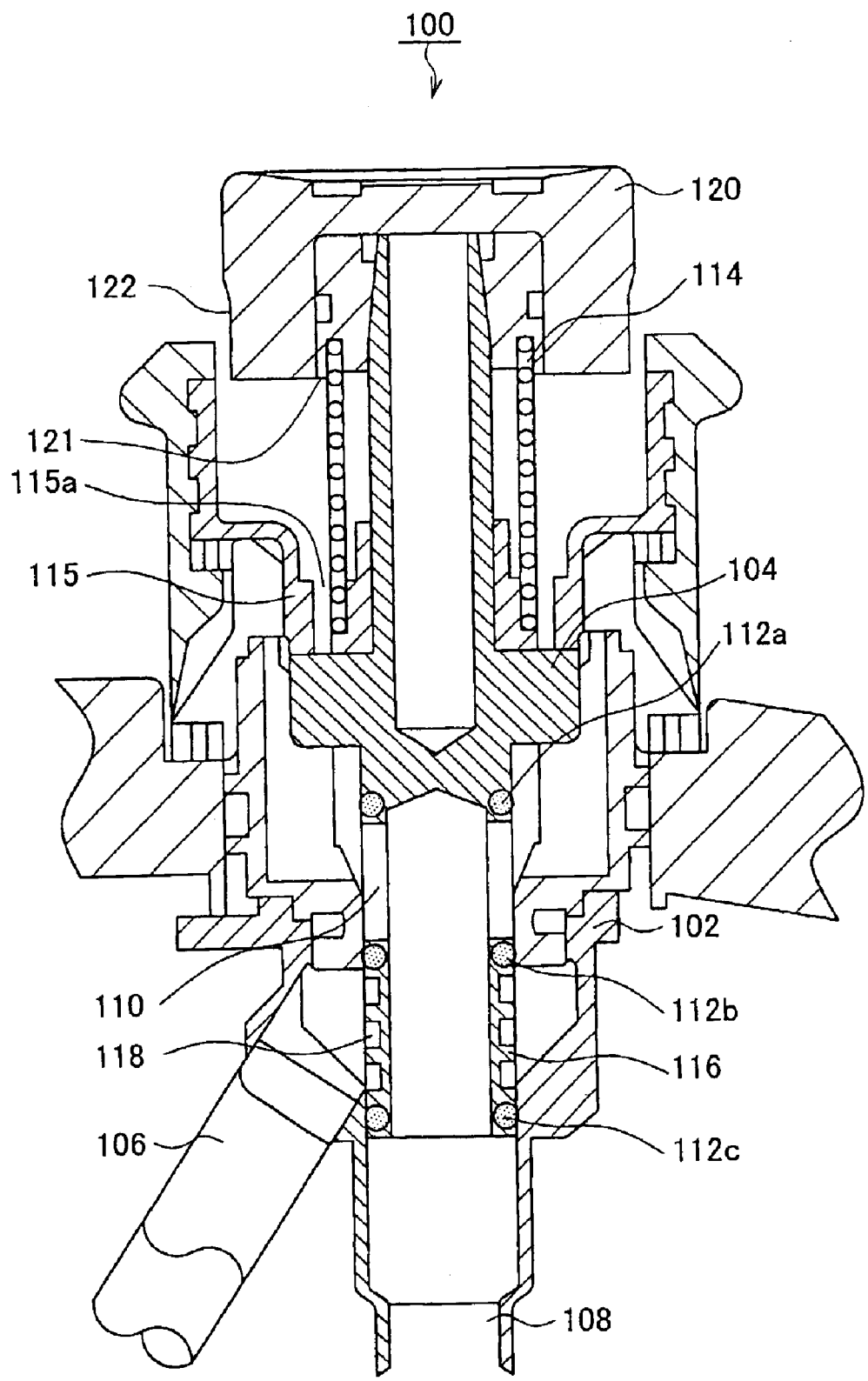
FIG. 1 is a sectional view of the suction valve embodied according to the invention, in the state where no sucking motion is carried out (referred to as "ordinary state" thereinafter).
Figure 2:
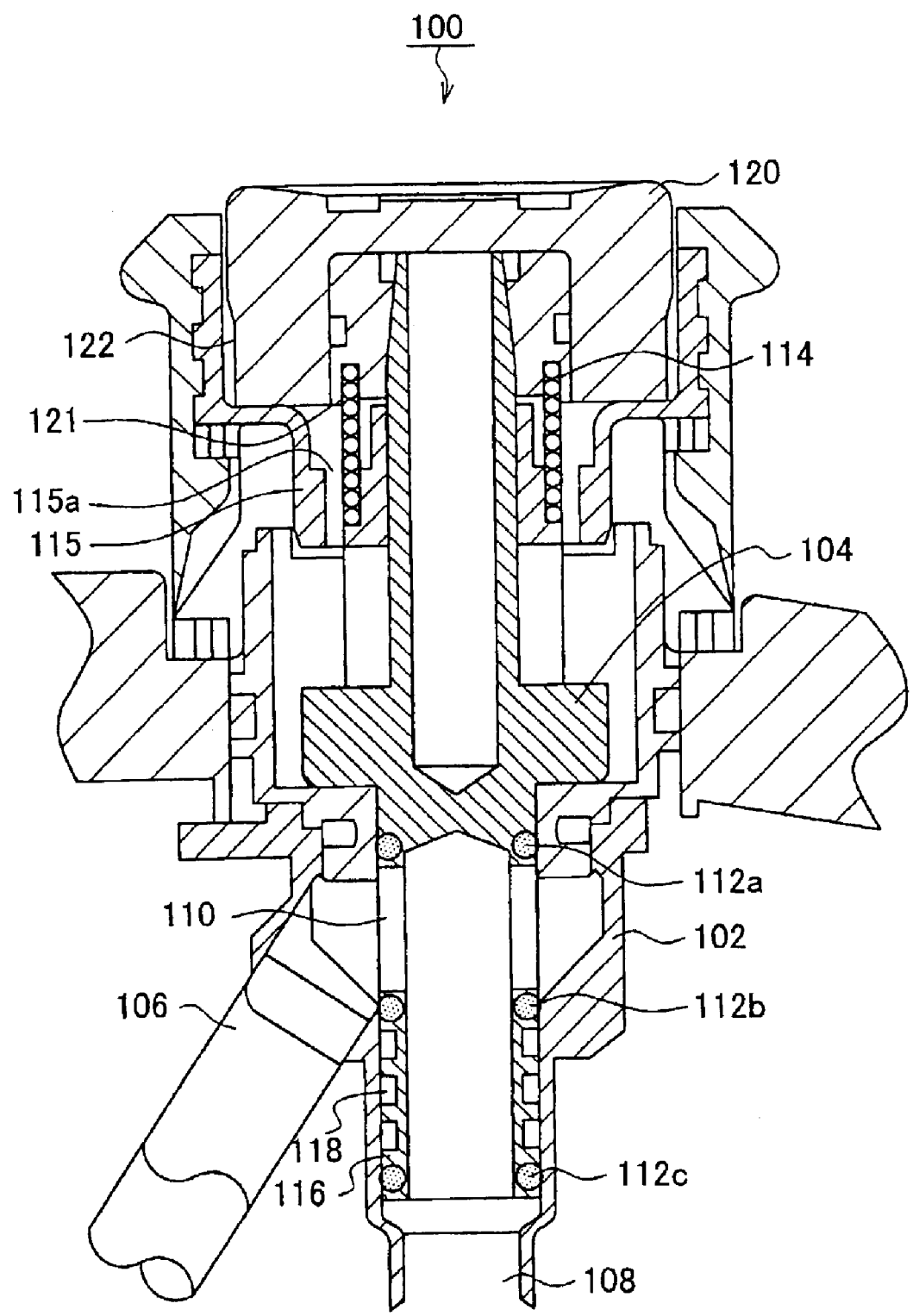
FIG. 2 is a sectional view of the suction valve embodied according to the invention, in the state where the suction control is carried out (referred to "suction control state" hereinafter).

First of all, let us describe the entire constitution of a suction valve for an endoscope use, especially medical use, according to the invention with reference to FIGS. 1 and 2. These figures are sectional views indicating the constitution of the suction valve for the endoscope use (referred to as "suction valve" simply hereinafter) according to an embodiment of the invention. FIG. 1 indicates a suction valve state wherein no suction control is carried out (ordinary state), in other words, the valve member is held in the suction cut-off position. FIG. 2 indicates a suction valve state wherein suction control is carried out (suction control state), in other words, the valve member is held in the suction control position.

A suction valve 100 according to the embodiment as shown in FIGS. 1 and 2 includes a valve casing 102 fitted to the control portion of the endoscope and a valve member 104 which is set up in the valve casing 102 so as to make a sliding motion in response to the push-down motion of a button 120.

The lower side face of the valve casing 102 is connected with one end of a suction side path 106, of which the other end opens as a suction inlet at the tip distal end portion of the endoscope, that is, the tip distal end of the insertion portion. Furthermore, the bottom portion of the valve casing 102 is connected with a suction source side path 108 which is connected with a negative pressure generation source for instance a suction pump (not shown).

An active blockade face 116 is formed in the outer peripheral surface around the lower part of the valve member 104 while a side through-hole 110 is formed on the upper side of the active blockade face 116. The bottom portion of the valve member 104 is kept open and is in communication with the above side through-hole 110.

In the vicinity of the side through-hole 110 on the outer peripheral surface of the valve member 104, for instance the upper and lower portions of the side through-hole 110, there are provided airtightness-holding members (sealing members) for instance O-rings 112a and 112b while another sealing member O-ring 112c is provided in the vicinity of the bottom portion of the valve member 104. Two O-rings 112b and 112c of the above three function as the airtightness-holding members provided on both of upper and lower ends of a portion which is defined on the outer peripheral surface of the valve member 104 to cut off the suction side path 106. That is, these O-rings 112a, 112b and 112c make it possible to maintain the airtightness of the sliding portion between the valve casing 102 and the active blockade face 116 of the valve member 104.

With the sliding motion of the valve member 104, the suction side path 106 and the suction source side path 108 are cut off from each other by the active blockade face 116 as indicated in FIG. 1 while they are communicated with each other via the side through-hole 110 of the valve member 104 as shown in FIG. 2.

Furthermore, the button 120 is provided with an energizing means for instance a spring 114, which energizes the valve member 104 moving together with the button 120 as one body upward with respect to the valve casing 102. To put it more concretely, the spring 114 is provided between the lower end portion 121 of the button 120 and a spring seat member 115.

The above spring seat member 115 has a communicating hole 115 formed therein. The outside peripheral surface of the button 120 includes a plurality of air releasing grooves 122 formed thereon at a predetermined interval. While the suction valve 100 is not in the suction control state (i.e. the valve member is held in the suction cut-off position as shown in FIG. 1), the suction source side path 108 connected with the negative pressure generation source (not shown) communicates with the atmosphere via the side through-hole 110 of the valve member 104, the hole 115a of the spring seat member 115 and air releasing grooves 122 of the button 120, respectively. As the result of this, the tip distal end opening portion of the endoscope communicating with the suction side path 106 is held in the substantially non-loaded state.

In this embodiment, the active blockade face 116 of the valve member 104 includes a plurality of grooves 118, which are formed in the active blockade face 116 such that foreign substances like blood and others sticking to the active blockade face can get into the grooves 118 with ease. To put it more concretely, the above grooves 118 are formed in the active blockade face 116 defined between the O-ring 112b at the lower end portion of the side through-hole 110 and the O-ring 112c provided in the vicinity of the bottom portion of the valve member 104.

Figure 3:
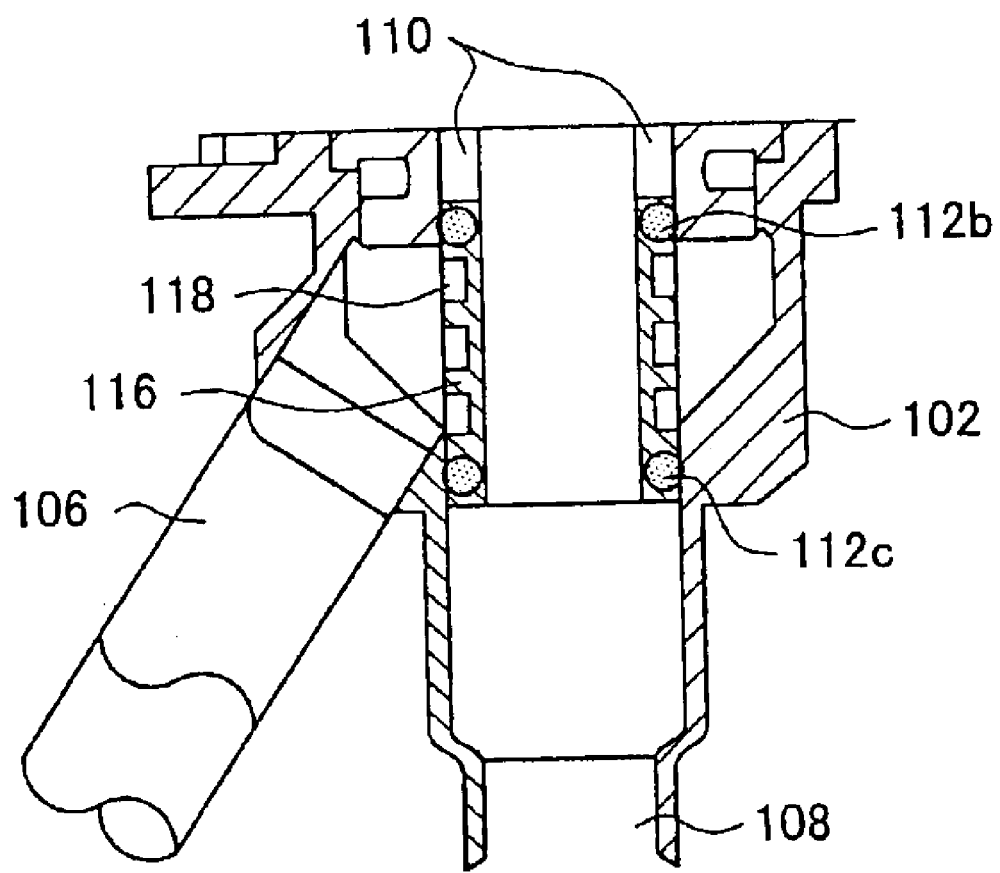
FIG. 3 is an enlarged view in the vicinity of an active blockade face of the suction valve embodied according to the invention, in the ordinary state.
Figure 4:
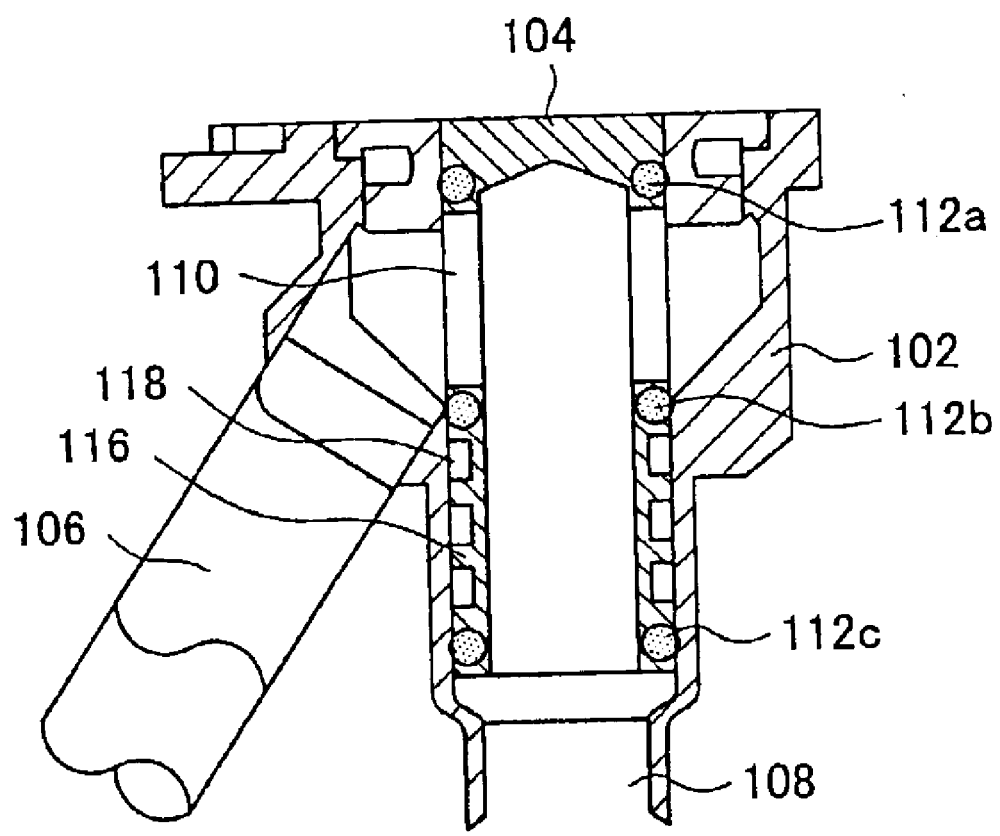
FIG. 4 is an enlarged view in the vicinity of an active blockade face of the suction valve embodied according to the invention, in the suction control state.

In the next, the function of the groove 118 formed in the valve member 104 of the suction valve 100 as mentioned above will be described with reference to the accompanying drawings. FIGS. 3 and 4 are enlarged views showing the portion in the vicinity of the active blockade face 116 of the valve member 104 in two states corresponding to those as shown in FIGS. 1 and 2, respectively. That is, FIG. 3 indicates the state in which the suction valve 100 is doing no sucking motion (ordinary state) while FIG. 4 indicates the state wherein the suction valve 100 is doing the suction control (suction control state).

In the state where no suction operation is carried out as shown in FIG. 3, even if foreign substances, blood and others still remain on the active blockade face 116 of the valve member 104, it is possible to drive the above foreign substances to the inside of the groove 118 and to make them stay there by pushing the button 120 downward by using the hand fingers so as to put the suction valve 100 in the state of suction operation as shown in FIG. 4.

Accordingly, even when making the suction side path 106 communicate with the suction source side path 108 by pushing down the suction valve 100, as the above foreign substances are driven to the inside of the groove 118, it is prevented that the slide friction of the slide portion between the inside surface of the valve casing 102 and the active blockade face 116 of the valve member 104 is increased due to the above foreign substances.

Figure 5A:
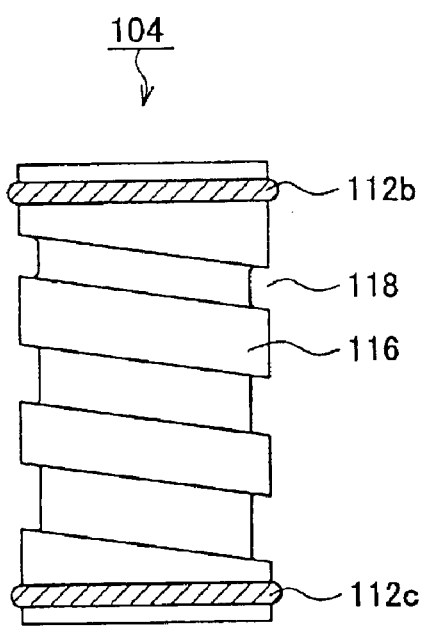
FIG. 5A is an exterior view of the grooves formed in the active blockade face of the suction valve embodied according to the invention.

Now, the shape of the groove 118 formed in the active blockade face 116 of the valve member 104 will be described with reference to the accompanying drawings. FIG. 5A is an illustration showing an outline of the constitution of the active blockade face 116 provided with grooves 118 while FIG. 5B is an illustration showing an example of the shape variation of the groove 118.

Figure 5B:
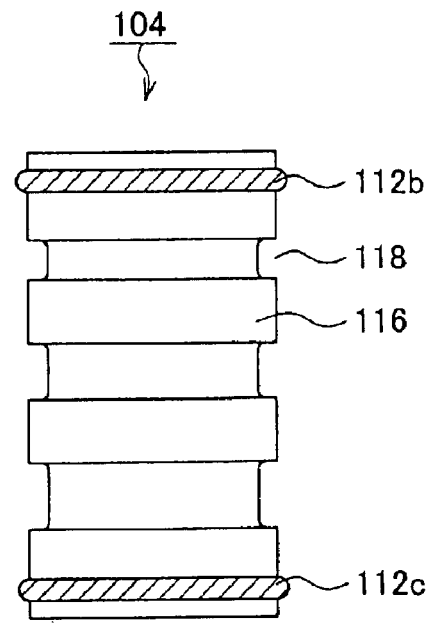
FIG. 5B is an exterior view showing variation of the grooves formed in the active blockade face of the suction valve embodied according to the invention.

The groove 118 formed in the active blockade face of the valve member 104 may have a spiral-like shape as shown in FIG. 5A or a circumference-like band as shown in FIG. 5B.

The spiral-like shaped groove 118 as shown in FIG. 5A can catch and remove the foreign substances sticking to the active blockade face 116 with ease more than the circumference-like shaped groove 118 as shown in FIG. 5B. Consequently, a larger amount of the foreign substances can be collected in the inside of the groove 118, thus it being prevented that the slide friction between the valve casing 102 and the active blockade face 116 is increased due to the above foreign substances.

Furthermore, as will be seen from FIGS. 5A and 5B, it is preferable that the width of groove 118 formed in the active blockade face is made wider along the direction of the suction source side path 108 (i.e. the downward direction in FIGS. 5A and 5B). With the constitution of the groove 118 like the above, repetition of suction switching operation causes the movement of the foreign substances sticking to the active blockade face 116 of the valve member 104 along the direction of the suction source side path 108 and enables the larger amount of the foreign substances to be stored in the groove 118.

Figure 6A:
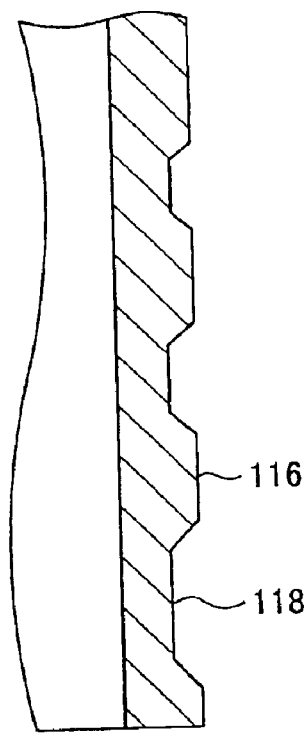
FIG. 6A is an exterior view of the grooves formed in the active blockade face of the suction valve embodied according to the invention.
Figure 6B:
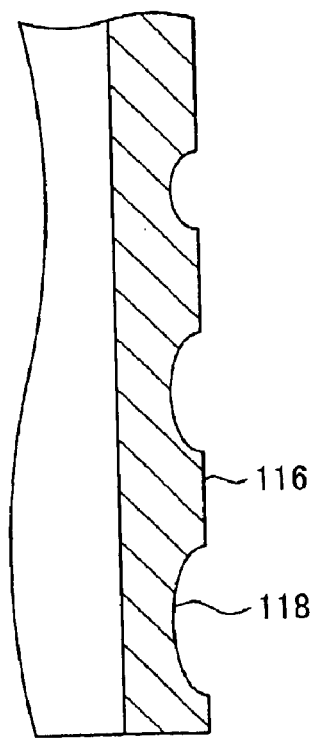
FIG. 6B is an exterior view showing another variation of the grooves formed in the active blockade face of the suction valve embodied according to the invention.
Figure 7:
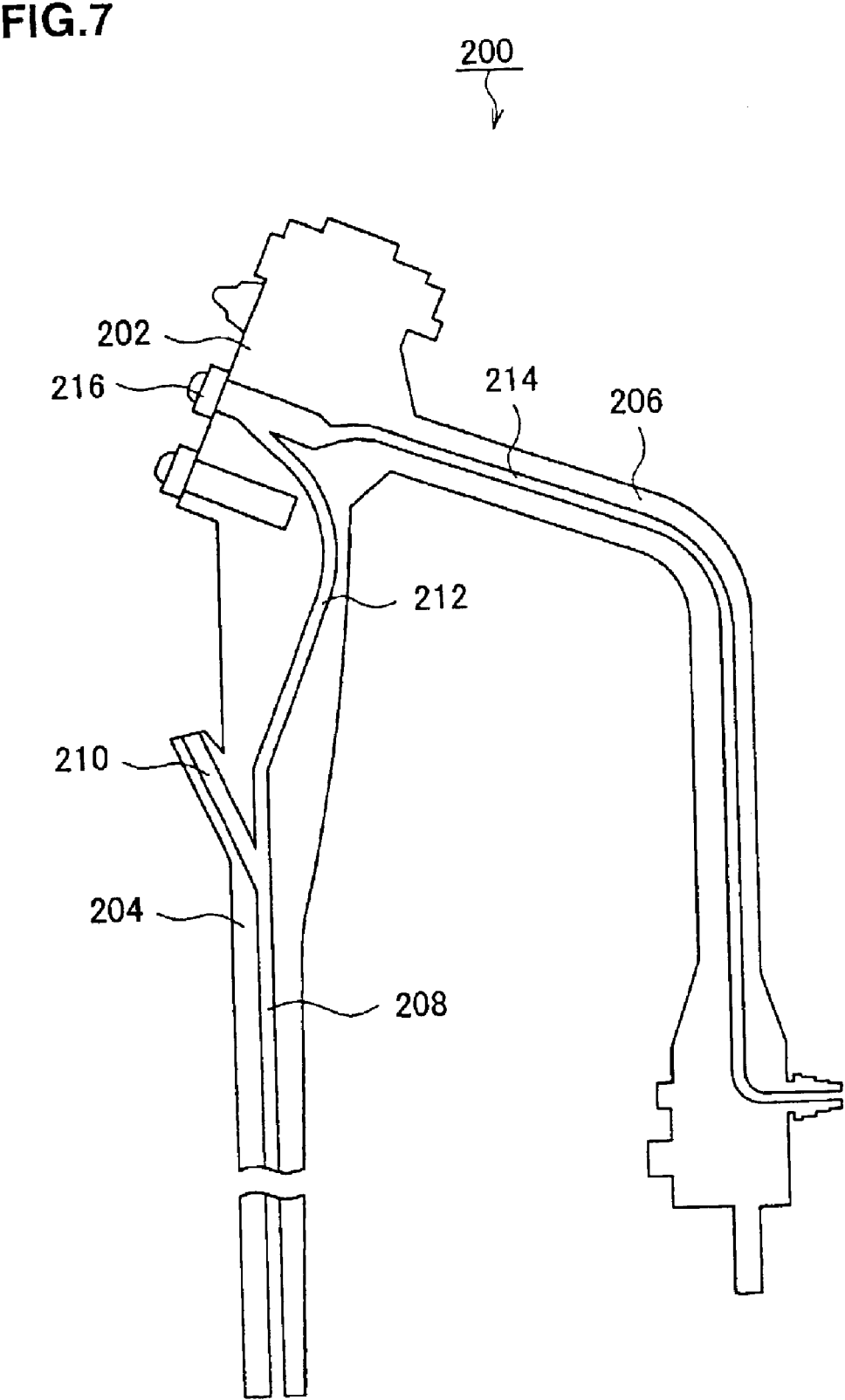
FIG. 7 is an illustration showing the entire constitution of an endoscope.
Figure 8:
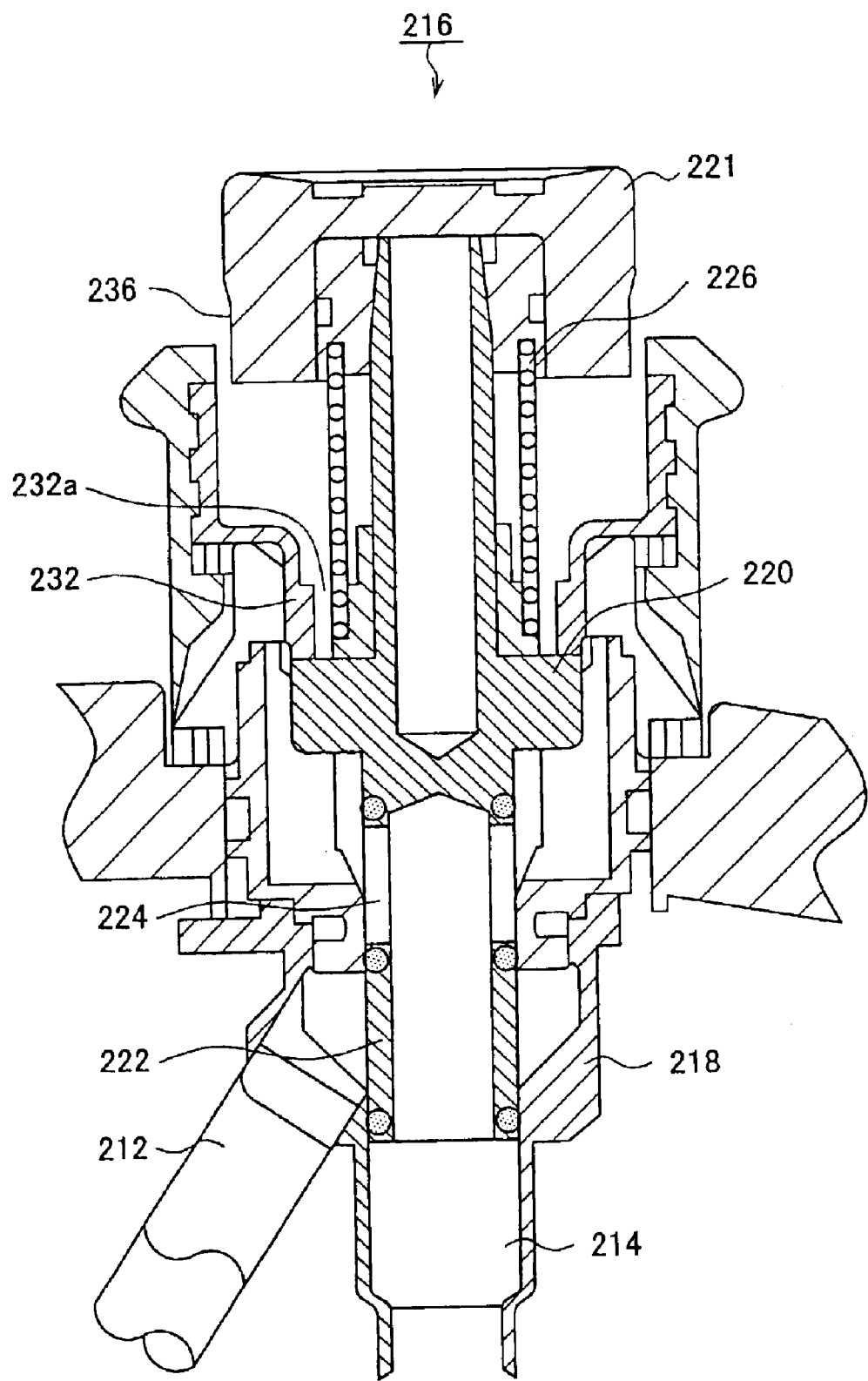
FIG. 8 is a sectional view of a prior art suction valve in the ordinary state.
Figure 9:
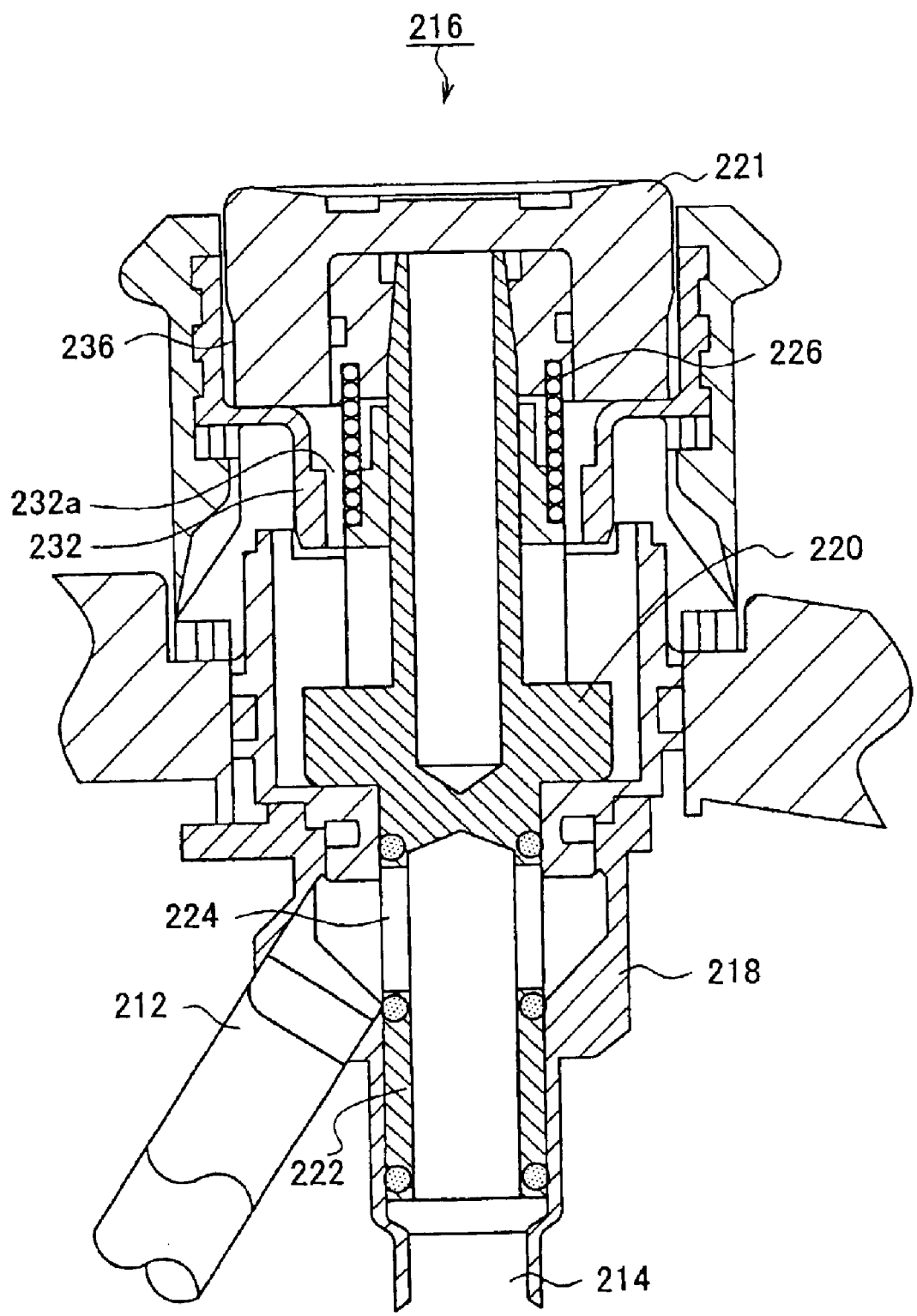
FIG. 9 is a sectional view of a prior art suction valve in the suction control state.

Still further, it is preferable that the sectional shape of the groove 118 formed in the active blockade face 116 is formed such that the width of its opening portion is longer than the depth of the same. The sectional shape may have a trapezoidal shape as shown in FIG. 6A or a curved shape for instance a semicircular shape, a semi-oval shape as shown in FIG. 6B and so forth. As the groove 118 formed in the active blockade face 116 is able to have variations with respect to the sectional shape thereof as described above, the foreign substances can be easily removed in the overhaul cleaning of the suction valve 100.

Still further, in order to efficiently make the foreign substances sticking to the active blockade face 118 move to and store them inside the groove 118 while the suction valve 100 carries out the suction switching control, it is preferable that the depth of the groove 118 of the active blockade face 116 is twice as large as or more than the gap width between the valve casing 102 and the active blockade face 116 of the valve member 104.

In the next, there will be described the suction control by means of the suction valve 100 as constituted according to the embodiment of the invention.

While the endoscope is used, the negative pressure generation source (not shown) connected with the suction source side path 108 is always kept in the active state. While no suction control is carried out, that is, in the ordinary state, the button 120 is not pushed downward as shown in FIG. 1. In this state, the suction side path 106 is cut off from the suction source side path 108 by the active blockade face 116 of the valve member 104, and the negative pressure generation source is in communication with the atmosphere through the suction valve 100. The suction inlet of the tip distal end of the insert portion in communication with the suction side path 106 is held in the substantially no-loaded state.

To the contrary, when starting the suction control of the endoscope, the button 120 is first pushed downward by using the hand fingers. With this pushing motion, the valve member 104 of the suction valve 100 slides downward along the valve casing 102. Thus, the valve member 104 is moved downward as shown in FIG. 2, thereby the suction side path 106 coming to communicate with the suction source side path 108 through the side through-hole 116 of the valve member 104. With this, the negative pressure suction force generated by the negative pressure generation source comes to act on the suction inlet of the tip distal end of the insertion portion.

After finishing a desired suction control, if the hand fingers are taken off from the push-and-move portion (i.e. button) 120 of the valve member 104, this valve member is pushed up by the energizing force of the spring 114 and returns to the ordinary state as shown in FIG. 1. With this, the suction side path 106 and the suction source side path 108 are cut off from each other by the active blockade face 116 of the valve member 104.

During the repetition of the suction control as mentioned above, it might take place that foreign substances for instance blood and others stick to the active blockade face 116 of the suction valve 100 while it stays in the ordinary state as shown in FIG. 1. However, the foreign substances could be moved to and stored inside the groove 118 formed in the active blockade face 116 whenever the suction valve 100 gets into the next suction control state. Accordingly, the increase in the slide friction due to the foreign substances creeping into the tiny gap between the valve casing 102 and the active blockade face 116 of the valve member 104 can be prevented and the smooth and stable suction control can be realized.

While preferred embodiments of the invention have been shown and described with reference to the accompanying drawings, it is needless to say that the invention should not be limited by these examples. It will be apparent to those skilled in the art that various changes and modifications can be made without departing from the principle and spirit of the invention, the scope of which is defined in the appended claims, and it is understood that those changes and modifications belong to the technical scope of the invention.

For instance, in the embodiment as described above, the groove 118 formed in the active blockade face 116 of the valve member 104 is formed to face in the direction perpendicular to the slide direction of the valve member 104 or to have a spiral-like shape, but formation of the groove 118 is not limited to these examples. The groove 118 may be formed to simply face in the oblique direction. Furthermore, the groove 118 may be formed by combining a plurality of grooves facing in the direction vertical to the slide direction of the valve member 104 and the groove facing in the oblique direction which is in communication with each of the above plural grooves.

Furthermore, as far as the groove 118 is formed within the active blockade face 116 defined between the O-ring 112c provided in a part on the side of the suction source side path 108 and the O-ring 112b provided in the vicinity of the side through-hole 110, even if the groove 118 is formed to face in the same direction as the slide direction of the valve member 104, the groove 118 can bring about the same effect as described above.

Still further, in the embodiment as has been discussed above, it has been explained that O-rings 112a, 112b and 112c are used as sealing members of the active blockade face 116 of the valve member 104, respectively. However, even if these sealing members are not arranged to the active blockade face 116, it is possible to make the active blockade face 116 of the valve member 104 work as a part of the sliding portion between the valve casing 102 and the active blockade face 116 of the valve member 104, thus enabling the groove 118 to be formed in that part.

As has been explained above, according to the invention, even if foreign substances for instance blood and others stick to the active blockade face of the valve member, it is prevented that the slide friction is increased due to the foreign substances remaining in the tiny gap between the valve casing and the active blockade face of the valve member, thus enabling the stable and smooth suction switch control to be realized and carried out.

What is claimed is:

1. A suction valve for an endoscope, comprising:
   a valve casing which is set up in a control portion of an endoscope and is connected with a suction side path having an opening as a suction inlet at the tip distal end of the insertion portion of said endoscope, and is also connected with a suction source side path connected with a negative pressure generation source;
   a valve member which is fitted up inside of said valve casing and being adapted to make a slide motion inside thereof and is constituted such that it is able to switch from a state in which said suction side path is cut off from said suction source side path, to a state in which said suction side path is in communication with said suction source side path or vice versa, in correspondence with a position of said valve member in said valve casing, said valve member having an outer peripheral surface that defines an active blockade face which is movable to be in front of an opening leading directly into the suction side path to seal off the suction side path; and a groove formed in the outer peripheral surface of said valve member which comes in contact with the inside of said valve casing, wherein said groove is formed in the active blockade face, so that when the active blockade face is moved to be in front of the opening, said groove is disposed in front of the opening to allow foreign substances in a region of the opening and from the suction side path to be accommodated within the groove.

2. A suction valve for an endoscope use as claimed in claim 1, wherein said valve member is constituted such that one state wherein said suction side path is cut off while said suction source side path is in communication with the atmosphere and the other state wherein said suction source side path is cut off from the communication with the atmosphere while the said suction source side path is in communication with said suction side path are switched from one to the other or vise versa corresponding to the position of said valve member in said valve casing.

3. A suction valve for an endoscope use as claimed in claim 1, wherein an airtightness-holding member is provided in order to hold the airtightness of a slide portion between said valve member and said valve casing, said airtightness-holding member being fitted into both ends of a part defined on the outer peripheral surface of said valve member to cut off said suction side path; and at least a groove is formed between said airtightness-holding members on the outer peripheral portion of said valve member.

4. A suction valve for an endoscope use as claimed in claim 1, wherein said groove is formed in the outer peripheral surface of said valve member and has a spiral-like shape.

5. A suction valve for an endoscope use as claimed in claim 1, wherein said groove is formed in the outer peripheral surface of said valve member and has a circumference-like band shape.

6. A suction valve for an endoscope use as claimed in claim 1, wherein said groove is formed in the outer peripheral surface of said valve member such that the nearer the groove approaches said suction source side path, the wider the width of it becomes.

7. A suction valve for an endoscope use as claimed in claim 1, wherein the depth of said groove is twice as large as or more than a gap width between the inside surface of said valve casing and the outer peripheral surface of said of said valve member.

8. A suction valve for an endoscope use as claimed in claim 1, wherein the section of said groove has such a shape that the opening portion of said groove becomes wider as the distance from the bottom of said groove becomes longer.

9. A suction valve for an endoscope use as claimed in claim 8, wherein the section of said groove has a trapezoidal shape.

10. A suction valve for an endoscope use as claimed in claim 8, wherein the section of said groove has a curved shape.

11. A suction valve for an endoscope, comprising:

a valve casing which is set up in a control portion of an endoscope and is connected with a suction side path having an opening as a suction inlet at the tip distal end of the insertion portion of said endoscope, and is also connected with a suction source side path connected with a negative pressure generation source;

a valve member which is fitted up inside of said valve casing and being adapted to make a slide motion inside thereof and is constituted such that it is able to switch from a state in which said suction side path is cut off from said suction source side path, to a state in which said suction side path is in communication with said suction source side path or vice versa, in correspondence with a position of said valve member in said valve casing; and a groove formed in the outer peripheral surface of said valve member which comes in contact with the inside of said valve casing;

wherein there are formed in the outer peripheral surface a plurality of grooves facing in at least one of a direction vertical to the slide direction of said valve member, and in an oblique direction with respect to the slide direction of said valve member.

12. A suction valve for an endoscope use as claimed in claim 1, wherein there are formed in the outer peripheral surface a plurality of grooves facing in the direction vertical to the slide direction of said valve member and there is additionally formed at least a groove facing in the oblique direction, which is in communication with each of the above plural grooves.

13. A suction valve for an endoscope use as claimed in claim 3, wherein said groove is formed along the slide direction of said valve member.

* * * * *